United States Patent
Sadakane et al.

(10) Patent No.: US 10,363,202 B2
(45) Date of Patent: Jul. 30, 2019

(54) DENTAL MATERIAL INCLUDING PROPYLBARBITURIC ACID POLYMERIZATION CATALYST

(71) Applicant: SHOFU INC., Kyoto (JP)

(72) Inventors: Yuji Sadakane, Kyoto (JP); Masako Shigezawa, Kyoto (JP); Yusei Kadobayashi, Kyoto (JP)

(73) Assignee: SHOFU INC., Kyoto (JP)

( * ) Notice: Subject to any disclaimer, the term of this patent is extended or adjusted under 35 U.S.C. 154(b) by 0 days.

(21) Appl. No.: 14/968,980

(22) Filed: Dec. 15, 2015

(65) Prior Publication Data

US 2016/0175203 A1 Jun. 23, 2016

(30) Foreign Application Priority Data

Dec. 17, 2014 (JP) ................................. 2014-255044
May 28, 2015 (JP) ................................. 2015-108190

(51) Int. Cl.
| | |
|---|---|
| *A61K 6/083* | (2006.01) |
| *C08F 4/54* | (2006.01) |
| *A61C 5/00* | (2017.01) |
| *A61K 6/00* | (2006.01) |
| *C08F 4/48* | (2006.01) |

(52) U.S. Cl.
CPC ............ *A61K 6/083* (2013.01); *A61K 6/0052* (2013.01); *C08F 4/48* (2013.01); *C08F 4/54* (2013.01)

(58) Field of Classification Search
None
See application file for complete search history.

(56) References Cited

U.S. PATENT DOCUMENTS

| | | | | |
|---|---|---|---|---|
| 5,407,973 A | * | 4/1995 | Hasegawa .............. | A61K 6/083 523/116 |
| 2010/0240797 A1 | | 9/2010 | Yarimizu et al. | |
| 2010/0249266 A1 | | 9/2010 | Yarimizu et al. | |
| 2015/0038614 A1 | * | 2/2015 | Sato ....................... | A61K 6/083 523/116 |

FOREIGN PATENT DOCUMENTS

| | | |
|---|---|---|
| JP | 6-345614 | 12/1994 |
| JP | 11-228330 | 8/1999 |
| JP | 2000-7518 | 1/2000 |
| JP | 2006-124412 | 5/2006 |
| JP | 2009-221171 | 10/2009 |
| JP | 2010-215824 | 9/2010 |
| JP | 2010-229165 | 10/2010 |
| JP | 2015-48328 | 3/2015 |
| JP | 5736086 | 6/2015 |

OTHER PUBLICATIONS

Extended European Search Report dated Apr. 6, 2016 in corresponding European Application No. 15199513.1.
Office Action dated Feb. 12, 2015 in corresponding Japanese Application No. 2014-255044, with English translation.
Office Action dated Jul. 8, 2015 in corresponding Japanese Application No. 2015-108190, with English translation.
Database WPI Week 200636, Thomson Scientific, 2006, XP002755819.
Database WPI Week 199944, Thomson Scientific, 1999, XP002755818.

* cited by examiner

*Primary Examiner* — Tae H Yoon
(74) *Attorney, Agent, or Firm* — Wenderoth, Lind & Ponack, L.L.P.

(57) ABSTRACT

The present invention relates to a polymerization catalyst having storage stability under an oral cavity environment. Furthermore, the present invention relates to a dental material cured by use of the present polymerization catalyst. The polymerization catalyst for use in the dental material is achieved with including 1-cyclohexyl-5-propylbarbituric acid and trioctylmethylammonium chloride.

11 Claims, 1 Drawing Sheet

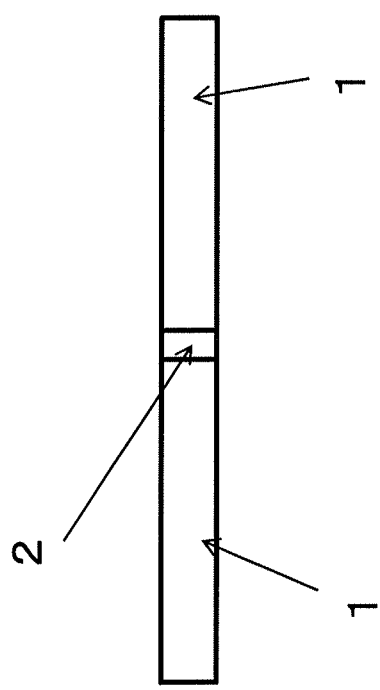

DENTAL MATERIAL INCLUDING PROPYLBARBITURIC ACID POLYMERIZATION CATALYST

BACKGROUND OF THE INVENTION

Field of the Invention

The present invention relates to a polymerization catalyst excellent in curability and discoloration resistance under an oral cavity environment and a dental material including the polymerization catalyst, as well as a dental powder-liquid type acrylic material excellent in curability and discoloration resistance under an oral cavity environment, for use in fabrication of a temporary inlay, a crown, a bridge and an individual tooth tray, and repair of a denture base.

Description of the Related Art

A benzoyl peroxide (BPO)/amine type catalyst has been conventionally used as a catalyst for room temperature polymerization utilized in the dental field. The BPO/amine type catalyst is poor in curability under the coexistence with an acidic compound, and a dental material using such a catalyst is easily changed in color over time. Therefore, another catalyst has been demanded. A catalyst including a combination of a barbituric acid compound and a halogen ion formation compound has been then developed. While the combination of a barbituric acid compound and a halogen ion formation compound, currently known, reduces discolorability of a dental material, it has caused the problem about curability of a dental material, which has not been solved, as compared with the BPO/amine type catalyst, and a polymerization catalyst excellent in curability has been demanded.

In particular, an oral cavity is usually at a constant temperature of 37° C., a dental material for use under an oral cavity environment is constantly under a bite pressure of even 40 to 50 kg, and a resin forming the dental material is constantly under a large load. Therefore, there is caused deterioration in physical properties of the dental material mounted in the oral cavity, and initial performances of the dental material cannot be maintained for a long time.

With respect to such conventional catalysts, for example, Japanese Patent Laid-Open No. 2010-229165 and Japanese Patent Laid-Open No. 2010-215824 describe the following: "n-cyclohexyl 5-ethylpyrimidinetrione" is used as a catalyst to thereby cure a resin. In addition, Japanese Patent Laid-Open No. 11-228330 and Japanese Patent Laid-Open No. 2000-007518 describe the following: "n-cyclohexyl 5-propylbarbituric acid" is used as a catalyst to thereby cure a resin. The catalysts in these patent documents, however, cannot impart excellent discoloration resistance of a dental material, and suppress deterioration in physical properties under an oral cavity environment.

As the above dental material, a dental powder-liquid type acrylic material is provided in which a catalyst can be compounded separately in a powder material of a (meth) acrylic polymer and a liquid material of a monomer, and the powder material and the liquid material can be kneaded to thereby initiate polymerization, providing a cured product. The cured product of the dental powder-liquid type acrylic material conventionally used, however, has been insufficient in bending strength of a polymer, and has not also been satisfactory in fillability in a prepared cavity.

In the case of filling a kneaded product of the conventional dental powder-liquid type acrylic material in a prepared cavity by use of a brush, the kneaded product of the dental powder-liquid type acrylic material is often released from the prepared cavity and attached to the brush. Furthermore, a denture base mounted in an oral cavity absorbs moisture in the oral cavity, and therefore, in the case of repair of such a denture base, wettability between the dental powder-liquid type acrylic material and the denture base is insufficient to often cause peeling of a portion repaired.

SUMMARY OF THE INVENTION

A polymerization catalyst has been demanded which not only overcomes the problem about discolorability of a dental material observed in the BPO/amine type catalyst, but also can improve curability of a dental material, which cannot be achieved by the combination of a barbituric acid compound and a halogen ion formation compound. In particular, a polymerization catalyst has been demanded which causes no deterioration in physical properties of a dental material even in use under an oral cavity environment, and a dental material using the polymerization catalyst has also been demanded which causes no deterioration in physical properties thereof.

In addition, a dental powder-liquid type acrylic material has been demanded in which, when a kneaded product of the dental powder-liquid type acrylic material is filled in a prepared cavity by use of a brush, the kneaded product can be well released from the brush and easily filled in the prepared cavity, and a cured article of the kneaded product can maintain an excellent bending property. Furthermore, a dental powder-liquid type acrylic material has been demanded in which, while an operation time required until the completion of filling in a prepared cavity and repair of a dental crown after kneading of a powder material and a liquid material of the dental powder-liquid type acrylic material is secured, curing rapidly progresses after the completion of filling and repair.

It has been found that a polymerization catalyst of 1-cyclohexyl-propylbarbituric acid and trioctylmethylammonium chloride is compounded for curing and thus a dental material achieves excellent discoloration resistance and allows physical properties not to be deteriorated even under an oral cavity environment.

It has been found that a polymerization catalyst of 1-cyclohexyl-propylbarbituric acid, trioctylmethylammonium chloride and an organometal compound is compounded for curing and thus a dental material achieves excellent discoloration resistance and allows physical properties not to be deteriorated even under an oral cavity environment.

It has been found that a polymerization catalyst of 1-cyclohexyl-propylbarbituric acid and trioctylmethylammonium chloride is applied to a dental material and therefore the dental material exhibits an excellent curing property and, in particular, allows reductions in bending strength and compressive strength to be alleviated.

It has been found that a polymerization catalyst of 1-cyclohexyl-propylbarbituric acid, trioctylmethylammonium chloride and an organometal compound is applied to a dental material and therefore the dental material exhibits an excellent curing property and, in particular, allows reductions in bending strength and compressive strength to be further alleviated.

It has also been found that the dental powder-liquid type acrylic material of the present invention can be attached on a wet tooth surface, does not cause discoloration, and allows reductions in bending strength and compressive strength to be alleviated.

The present invention provides a polymerization catalyst for a dental material that is a polymerization catalyst for use in a dental material, including 1-cyclohexyl-5-propylbarbituric acid and trioctylmethylammonium chloride. Furthermore, the polymerization catalyst for a dental material preferably includes an organometal compound.

The present invention also provides a dental material using the polymerization catalyst for a dental material.

The dental material preferably includes a filler, and the amount of the filler to be compounded is preferably 1 to 2000 parts by weight based on 100 parts by weight of a polymerizable monomer.

A dental material cured by use of such a polymerization catalyst can exhibit a preferable curing property.

The dental powder-liquid type acrylic material of the present invention can achieve an object by kneading of a specific liquid material and a specific powder material in a certain ratio. The liquid material includes 100 parts by weight of a monomer and 0.1 to 10 parts by weight of trioctylmethylammonium chloride, and the powder material includes 70 to 130 parts by weight of a (meth)acrylic acid (co)polymer, 0.001 to 1 part by weight of the organometal compound and 0.1 to 10 parts by weight of 1-cyclohexyl-5-propylbarbituric acid based on 100 parts by weight of the monomer included in the liquid material.

Furthermore, the monomer in the liquid material preferably includes a (meth)acrylic acid group-containing monomer and/or a hydrophilic monomer, and the amount of the (meth)acrylic acid group-containing monomer to be compounded is 80 to 95 parts by weight and the amount of the hydrophilic monomer to be compounded is 5 to 20 parts by weight. In addition, the liquid material includes 0.5 to 20 parts by weight of an organic solvent based on 100 parts by weight of the monomer.

Compounding of the liquid material and the powder material is conducted by kneading in a weight ratio of 1:0.8 to 1.2, preferably 1:0.95 to 1.05, further preferably 1:1.

According to the polymerization catalyst of the present invention, a dental material compounded therewith can be excellent in discoloration resistance and can allow deterioration in physical properties under an oral cavity environment to be suppressed.

According to the dental material of the present invention, excellent discoloration resistance can be achieved and deterioration in physical properties under an oral cavity environment can be suppressed.

The dental powder-liquid type acrylic material of the present invention can be well released from a brush, and easily filled in a prepared cavity. In addition, the dental powder-liquid type acrylic material can allow a time, which can be taken for appropriately conducting a dental treatment, to be secured, and can be excellent in curability after curing and therefore can allow final finish such as polishing to be easily performed.

Furthermore, the dental powder-liquid type acrylic material easily reaches a state of a uniform rice cake after kneading of the powder material and the liquid material, and is kept in the same state for a certain time and is also good in operationability in an oral cavity.

While production of a temporary inlay, a crown and a bridge, which is a working in an oral cavity, is a working in the wet state, even a prosthetic appliance fabricated under such a wet environment is hardly deteriorated in terms of physical properties by means of the dental powder-liquid type acrylic material of the present invention.

DETAILED DESCRIPTION OF THE PREFERRED EMBODIMENTS

[Polymerization Catalyst]

The polymerization catalyst of the present invention includes 1-cyclohexyl-5-propylbarbituric acid and trioctylmethylammonium chloride.

(1-Cyclohexyl-Propylbarbituric Acid)

The amount of 1-cyclohexyl-propylbarbituric acid to be compounded is preferably 0.1 to 10 parts by weight based on 100 parts by weight of a polymerizable monomer. The amount to be compounded is further preferably 0.5 to 5 parts by weight, still further preferably 1 to 3.0 parts by weight. If the amount to be compounded is less than 0.1 parts by weight, a case may occur in which reactivity is poor and a curable dental material cannot be obtained. If the amount to be compounded is more than 10 parts by weight, the amount of heat generation in a polymerization reaction may be remarkably large regardless of a certain curing time.

(Trioctylmethylammonium Chloride)

The amount of trioctylmethylammonium chloride to be compounded is preferably 0.1 to 10 parts by weight based on 100 parts by weight of a polymerizable monomer. The amount to be compounded is further preferably 0.5 to 5 parts by weight, still further preferably 1 to 3.0 parts by weight. If the amount to be compounded is less than 0.1 parts by weight, a case may occur in which reactivity is poor and a curable dental material cannot be obtained. If the amount to be compounded is more than 10 parts by weight, the amount of heat generation in a polymerization reaction may be remarkably large regardless of a certain curing time.

(Organometal Compound)

An organometal compound includes copper(II) acetylacetonate, acetylacetone copper, copper 4-cyclohexylbutyrate, cupric acetate, copper oleate, copper gluconate, acetylacetone manganese, manganese naphthenate, manganese octylate, acetylacetone cobalt(III), cobalt naphthenate, acetylacetone lithium, lithium acetate, acetylacetone zinc, zinc naphthenate, acetylacetone nickel, nickel acetate, acetylacetone aluminum, acetylacetone calcium, acetylacetone chromium(III), acetylacetone iron(III), sodium naphthenate and rare earth octoate, and these may be used singly or as a mixture of two or more. Copper(II) acetylacetonate, acetylacetone copper and copper 4-cyclohexylbutyrate are particularly preferable.

The amount of such an organometal compound to be compounded is 0.001 to 1 part by weight, preferably 0.001 to 0.2 parts by weight based on 100 parts by weight of a polymerizable monomer. If the amount to be compounded is less than 0.001 parts by weight, a case may occur in which reactivity is poor and a curable dental material cannot be obtained. If the amount to be compounded is more than 1 part by weight, discoloration unique to the organometal compound is remarkable, and if the amount to be compounded is more than 0.2 parts by weight, a case may occur in which such discoloration is observed. For example, when the organometal compound is acetylacetone copper, a blue color is displayed, and when the organometal compound is acetylacetone iron(III), a red-brown color is displayed.

[Dental Material]

The dental material to which the polymerization catalyst of the present invention is applied means a dental treatment material that is finally used in an oral cavity, and means a material that is used by a dentist in a treatment and a resin type material that is produced by a dental technician for a treatment. Specifically, the dental material includes a composite resin, an adhesive, a resin cement, a base resin, a facing crown, an orthotic material, an artificial tooth, a sealer, a temporary sealing material, a temporary adhesion material and a temporary denture.

The polymerizable monomer for use in the dental material to which the polymerization catalyst of the present invention is applied is not particularly limited as long as it is a polymerizable monomer having a polymerizable group. Specifically, known monofunctional and/or multifunctional polymerizable monomer(s) commonly used for a dental material can be used. A preferable polymerizable monomer is a (meth)acrylic acid group-containing polymerizable monomer having acryloyl group and/or methacryloyl group(s). Next, specific names of the polymerizable monomer are described. Herein, (meth)acrylate or (meth)acryloyl may comprehensively designate both of an acryloyl group-containing polymerizable monomer and a methacryloyl group-containing polymerizable monomer.

((Meth)Acrylic Acid Group-Containing Polymerizable Monomer)

Examples of the (meth)acrylic acid group-containing polymerizable monomer include:

monofunctional monomers (uncrosslinkable monomers): (meth)acrylates such as methyl (meth)acrylate, ethyl (meth)acrylate, butyl (meth)acrylate, hexyl (meth)acrylate, tetrahydrofurfuryl (meth)acrylate, 2-hydroxyethyl (meth)acrylate, glycidyl (meth)acrylate, lauryl (meth)acrylate, cyclohexyl (meth)acrylate, benzyl (meth)acrylate, allyl (meth)acrylate, 2-ethoxyethyl (meth)acrylate, methoxypolyethylene glycol (meth)acrylate, glycerol (meth)acrylate and isobonyl (meth)acrylate; silane compounds such as γ-(meth)acryloyloxypropyltrimethoxysilane and γ-(meth)acryloyloxypropyltriethoxysilane; and nitrogen-containing compounds such as 2-(N,N-dimethylamino)ethyl (meth)acrylate, N-methylol (meth)acrylamide and diacetone (meth)acrylamide, aromatic bifunctional monomers (crosslinkable monomers): 2,2-bis(4-(meth)acryloyloxyphenyl)propane, 2,2-bis(4-(3-(meth)acryloyloxy-2-hydroxypropoxy)phenyl) propane, 2,2-bis(4-(meth)acryloyloxyethoxyphenyl)propane, 2,2-bis(4-(meth)acryloyloxydiethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2(4-(meth)acryloyloxyethoxyphenyl)-2(4-(meth)acryloyloxydiethoxyphenyl)propane, 2(4-(meth)acryloyloxydiethoxyphenyl)-2(4-(meth)acryloyloxytriethoxyphenyl)propane, 2(4-(meth)acryloyloxydipropoxyphenyl)-2(4-(meth)acryloyloxytriethoxyphenyl)propane, 2,2-bis(4-(meth)acryloyloxydipropoxyphenyl)propane and 2,2-bis(4-(meth)acryloyloxyisopropoxyphenyl)propane, aliphatic bifunctional monomers (crosslinkable monomers): 2-hydroxy-3-acryloyloxypropyl methacrylate, hydroxypivalic acid neopentyl glycol di(meth)acrylate, ethylene glycol di(meth)acrylate, diethylene glycol di(meth)acrylate, triethylene glycol di(meth)acrylate, butylene glycol di(meth)acrylate, polyethylene glycol di(meth)acrylate, neopentyl glycol di(meth)acrylate, propylene glycol di(meth)acrylate, 1,3-butanediol di(meth)acrylate, 1,4-butanediol di(meth)acrylate, 1,6-hexanediol di(meth)acrylate and glycerin di(meth)acrylate, trifunctional monomers (crosslinkable monomers): trimethylolpropane tri(meth)acrylate, trimethylolethane tri(meth)acrylate, trimethylolmethane tri(meth)acrylate and pentaerythritol tri(meth)acrylate, and tetrafunctional monomers (crosslinkable monomers): pentaerythritol tetra(meth)acrylate and ditrimethylolpropane tetra(meth)acrylate.

(Urethane Type Polymerizable Monomer)

Examples of a urethane type polymerizable monomer include di(meth)acrylates having a bifunctional or tri- or higher functional urethane bond, derived from an adduct of a hydroxyl group-containing polymerizable monomer such as 2-hydroxyethyl (meth)acrylate, 2-hydroxypropyl (meth)acrylate or 3-chloro-2-hydroxypropyl (meth)acrylate and a diisocyanate compound such as methylcyclohexane diisocyanate, methylenebis(4-cyclohexylisocyanate), hexamethylene diisocyanate, trimethylhexamethylene diisocyanate, isophorone diisocyanate, diisocyanate methyl methylbenzene or 4,4-diphenylmethane diisocyanate.

As the polymerizable monomer for use in the dental material to which the polymerization catalyst of the present invention is applied, a polymerizable monomer other than the above (meth)acrylate type polymerizable monomers, such as a monomer, oligomer or polymer having at least one polymerizable group in the molecule, may be used depending on the intended use. The polymerizable monomer other than the (meth)acrylate type polymerizable monomers may have a substituent such as an acidic group and a fluoro group in one molecule. In the present invention, the polymerizable monomer may be a single component or may be a polymerizable monomer mixture including a plurality of polymerizable monomers. When the viscosity of the polymerizable monomer is extremely high at room temperature or the polymerizable monomer is a solid, the polymerizable monomer is preferably combined with a polymerizable monomer low in viscosity and used as a polymerizable monomer mixture. In such a combination, the polymerizable monomer may be used in combinations of two, or three or more.

The polymerizable monomer for use in the dental material to which the polymerization catalyst of the present invention is applied may include only a monofunctional polymerizable monomer, or may further include a multifunctional polymerizable monomer. A preferable polymerizable monomer includes an aromatic compound of a bifunctional polymerizable monomer and an aliphatic compound of a bifunctional polymerizable monomer. A more preferable polymerizable monomer includes 2,2-bis(4-(3-methacryloyloxy-2-hydroxypropoxy)phenyl)propane (Bis-GMA) and triethylene glycol dimethacrylate (TEGDMA).

In the present invention, the polymerizable monomer may include a polymerizable monomer containing an acid group such as a phosphoric acid group, a carboxylic acid group, a phosphonic acid group or a sulfonic acid group in the molecule, as all or part of the polymerizable monomer, in order to impart adhesiveness to a tooth substance or a base metal to the dental material to which the polymerization catalyst of the present invention is applied. In order to enhance adhesiveness to a noble metal, the polymerizable monomer in the present invention may include a polymerizable monomer containing a sulfur atom in the molecule.

Such a polymerizable monomer containing an acid group such as a phosphoric acid group, a carboxylic acid group, a phosphonic acid group or a sulfonic acid group in the molecule or containing a sulfur atom in the molecule is preferably compounded in a proportion of 0.5 to 20% relative to 100% of the polymerizable monomer.

Such a polymerizable monomer includes:

carboxylic acid group-containing polymerizable monomers: (meth)acrylic acid, 1,4-di(meth)acryloyloxyethylpyromellitic acid, 6-(meth)acryloyloxynaphthalene-1,2,6-tricarboxylic acid, N-(meth)acryloyl-p-aminobenzoic acid, N-(meth)acryloyl-5-aminosalicylic acid, 4-(meth)acryloyloxyethyltrimellitic acid and anhydride thereof, 4-(meth)acryloyloxybutyltrimellitic acid and anhydride thereof, 2-(meth)acryloyloxybenzoic acid, β-(meth)acryloyloxyethyl hydrogen succinate, β-(meth)acryloyloxyethyl hydrogen maleate, 11-(meth)acryloyloxy-1,1-undecanedicarboxylic acid and p-vinylbenzoic acid, polymerizable monomers containing a phosphoric acid group in the molecule, such as 2-(meth)acryloyloxyethyl dihydrogen phosphate, 3-(meth)acryloyloxypropyl dihydrogen phosphate, 10-(meth)acryloyloxydecyl dihydrogen phosphate, bis(2-(meth)acryloyloxyethyl) hydrogen phosphate and 2-(meth)acryloyloxyethylphenyl hydrogen phosphate, polymerizable monomers containing a sulfonic acid group in the molecule, such as 2-(meth)acrylamide-2-methylpropanesulfonic acid, 4-(meth)acryloyloxybenzenesulfonic acid and 3-(meth)acryloyloxypropanesulfonic acid, and polymerizable monomers containing a sulfur atom in the molecule, such as (meth)acrylate having a triazinethiol group, (meth)acrylate having a mercapto group, (meth)acrylate having a polysulfide group, (meth)acrylate having a thiophosphoric acid group, (meth)acrylate having a disulfide cyclic group, (meth)acrylate having a mercaptodithiazol group, (meth)acrylate having a thiouracil group and (meth)acrylate having a thiirane group. These polymerizable monomers may be used singly or as a mixture of two or more.

The filler to be compounded to the dental material to which the polymerization catalyst of the present invention is applied is not particularly limited, and a known filler, such as an inorganic filler and/or an organic filler and/or an organic-inorganic composite filler, can be used without any limitation. The shape of the filler before a silane treatment may be any particle shape such as a spherical shape, a massive shape, a needle shape, a plate shape, a fracture shape or a scale-like shape, and is not particularly limited. In order to achieve more stability of a paste, the filler preferably has a spherical shape. The degree of circularity indicating the spherical shape of the filler is in the range from 0.7 to 1.0, more preferably in the range from 0.9 to 1.0, further preferably in the range from 0.95 to 1.00.

With respect to the calculation method of the degree of circularity, the degree of circularity can be determined by processing an image taken by an optical microscope or a scanning electron microscope (hereinafter, referred to as SEM) by use of an image analysis apparatus. The number of samples to be image-processed is 50 or more, and the degree of circularity is calculated from the area of the filler and the boundary length of the filler. The calculation expression is the degree e of circularity=$(4 \cdot \pi \cdot S)/(L^2)$, and the degree of circularity is calculated from the area S of the filler and the boundary length L of the filler obtained from the image processing.

Specific examples of the inorganic filler include quartz, amorphous silica, aluminum silicate, aluminum oxide, titanium oxide, zirconium oxide, various glasses (including a glass by a melting method, a synthetic glass by a sol-gel method, and a glass produced by a gas phase reaction), calcium carbonate, talc, kaolin, clay, mica, aluminum sulfate, calcium sulfate, barium sulfate, calcium phosphate, hydroxyapatite, silicon nitride, aluminum nitride, titanium nitride, silicon carbide, boron carbide, calcium hydroxide, strontium hydroxide and zeolite. Among them, an aluminosilicate glass, borosilicate, aluminoborate and boroaluminosilicate glasses, and the like including sodium, strontium, barium, a heavy metal such as lanthanum, and/or fluorine are preferable. The average particle size of such an inorganic filler is not particularly limited, and is preferably in the range from 0.5 to 10 μm, more preferably in the range from 0.7 to 5 μm.

An ultrafine particle inorganic filler such as Aerosil produced by a gas phase method or a silica-zirconia oxide particle produced in a solution of a sol-gel reaction or the like can also be used. A cohesive inorganic filler in which such ultrafine particles aggregate, or the like is also used without any problem. In kneading of a composite material, when the cohesive inorganic filler is crushed so as to have an average particle size of 1 nm to 300 nm, it is classified into the ultrafine particle inorganic filler, and when the cohesive inorganic filler is not crushed so as to have an average particle size of 1 nm to 300 nm, it is classified into the inorganic filler.

The ultrafine particle inorganic filler is, but not limited, preferably colloidal silica (product name: Aerosil R972, Aerosil 200, Aerosil 380 or Aerosil 50 manufactured by Nippon Aerosil Co., Ltd., 5 to 50 nm).

The organic filler can be obtained by polymerizing a monomer having a polymerizable group, and the type thereof is not particularly limited. Specific examples of the organic filler include polymethyl methacrylate, and products obtained by (co)polymerization of a monomer having a polymerizable group described below singly or in combinations of two or more. Examples of the monomer having a polymerizable group include unsaturated aromatics such as styrene, α-methylstyrene, halogenated styrene and divinylbenzene; unsaturated esters such as vinyl acetate and vinyl propionate; unsaturated nitriles such as acrylonitrile; and butadiene or isoprene. The above-mentioned monomer having a polymerizable group, already known in the dental field, is particularly preferable. The method for producing the organic filler is not particularly limited, and any method such as emulsion polymerization, suspension polymerization or dispersion polymerization of the monomer having a polymerizable group, or a method for pulverizing a polymer bulk previously produced can also be conducted. An organic-inorganic composite filler in which an organic polymer contains an inorganic particle can also be used. The inorganic particle contained in the organic polymer is not particularly limited and a known particle can be used therefor, and examples include the inorganic fillers described above. The method for producing the organic-inorganic composite filler is not particularly limited, and any method can also be adopted. Examples include a method including subjecting the surface of the inorganic particle to microencapsulation or grafting by an organic substance, a method including introducing a polymerizable functional group or a polymerizable initiation group to the surface of the inorganic particle and then subjecting the resultant to radical polymerization, and a method including pulverizing a polymer bulk including the inorganic particle, previously produced.

The average particle size of the organic filler or the organic-inorganic composite filler is preferably in the range from 1 to 100 μm, more preferably 3 to 50 μm, further preferably 5 to 30 μm. Such inorganic, organic and organic-inorganic composite fillers can be each used singly or in combinations of several types.

The filler such as the inorganic, organic and organic-inorganic composite fillers can be used with the particle surface thereof being subjected to a surface treatment by a known method. Examples include a surfactant, an aliphatic acid, an organic acid, an inorganic acid, a silane coupling agent, a titanate coupling agent and polysiloxane. Such a surface treatment method is preferable from the viewpoints of enhancing wettability between a resin component and the filler surface and imparting various excellent characteristics, and the surface treatment can be appropriately selected depending on the characteristics demanded. The filler surface is subjected to a surface treatment by a special surface treatment agent and/or a special surface treatment method for the purpose of multi-functionalizing the filler, without any limitation.

The amount of the filler to be compounded depends on the type of the dental material, and is preferably 1 to 2000 parts by weight based on 100 parts by weight of the polymerizable monomer.

[Dental Powder-Liquid Type Acrylic Material]

The dental powder-liquid type acrylic material of the present invention is used with a liquid material and a powder material being kneaded. The liquid material and the powder material can be separately stored to result in an increase in shelf life. The liquid material and the powder material are kneaded to thereby initiate a curing reaction, and therefore the dental powder-liquid type acrylic material can be cured after a certain time. Specifically, for example, the liquid material includes a polymerizable monomer and trioctylmethylammonium chloride, and the powder material includes a (meth)acrylic acid (co)polymer, an organometal compound and 1-cyclohexyl-5-propylbarbituric acid. More specifically, for example, the liquid material includes 100 parts by weight of the monomer and 0.1 to 10 parts by weight of trioctylmethylammonium chloride, and the powder material includes 70 to 130 parts by weight of the (meth)acrylic acid (co)polymer, 0.001 to 1 part by weight of the organometal compound and 0.1 to 10 parts by weight of 1-cyclohexyl-5-propylbarbituric acid.

With respect to the method of kneading the powder material and the liquid material, the powder material and the liquid material can be loaded into a small container and kneaded by a brush, or a brush can be impregnated with the liquid material and thereafter brought into contact with the powder material to thereby swell the powder material, thereby providing the same kneaded product as the kneaded product of the liquid material and the powder material. The kneading method in which a brush is used can easily provide the kneaded product of the liquid material and the powder material.

The polymerizable monomer for use in the dental powder-liquid type acrylic material of the present invention is not particularly limited as long as the polymerizable monomer has a polymerizable group, and the polymerizable monomer described in the section [dental material] above can be used.

The (meth)acrylic acid group-containing polymerizable monomer for use in the dental powder-liquid type acrylic material of the present invention may be a single component or may be a kneaded product of a plurality of (meth)acrylic acid group-containing polymerizable monomers. A preferable (meth)acrylic acid group-containing polymerizable monomer can include a crosslinkable polymerizable monomer. A more preferable (meth)acrylic acid group-containing polymerizable monomer includes methyl (meth)acrylate (MMA) and both or any one of 1,6-hexanediol di(meth)acrylate (HDDMA) and triethylene glycol dimethacrylate (TEGDMA).

In the dental powder-liquid type acrylic material of the present invention, the polymerizable monomer preferably includes the (meth)acrylic acid group-containing polymerizable monomer and/or a hydrophilic polymerizable monomer. The hydrophilic polymerizable monomer has at least one hydroxyl group and at least one polymerizable unsaturated group in one molecule, is not particularly limited, and can be appropriately selected from known compounds depending on the intended use. The term hydrophilicity means a solubility in water of 50 [g/100 g-$H_2O$] or more at 20° C., and the hydrophilic polymerizable monomer is preferably compatible with water in any proportion at 20° C.

The hydrophilic polymerizable monomer can be compounded to result in an enhancement in wettability to a denture base that is mounted in an oral cavity and absorbs water, in the case of repair of the denture base.

Specific examples of the hydrophilic polymerizable monomer include 2-hydroxyethyl (meth)acrylate, 3-hydroxypropyl (meth)acrylate, 2-hydroxypropyl (meth)acrylate, 4-hydroxybutyl (meth)acrylate, N-2-hydroxyethyl (meth)acrylamide, N,N-bis(2-hydroxyethyl) (meth)acrylamide, 2,3-dihydroxypropyl (meth)acrylate, 2,3-dihydroxybutyl (meth)acrylate, 2,4-dihydroxybutyl (meth)acrylate, 2-hydroxymethyl-3-hydroxypropyl (meth)acrylate, 2,3,4-trihydroxybutyl (meth)acrylate, 2,2-bis(hydroxymethyl)-3-hydroxypropyl (meth)acrylate, 2,3,4,5-tetrahydroxypentyl (meth)acrylate, diethylene glycol mono(meth)acrylate, triethylene glycol mono(meth)acrylate, tetraethylene glycol mono(meth)acrylate, pentaethylene glycol mono(meth)acrylate and N-methylol(meth)acrylamide. Among them, 2-hydroxyethyl (meth)acrylate is most preferable.

The hydrophilic polymerizable monomer can be compounded singly, or can be used as a kneaded product of a plurality thereof.

Furthermore, the amount of the (meth)acrylic acid group-containing polymerizable monomer to be compounded is 80 to 95 parts by weight and the amount of the hydrophilic polymerizable monomer to be compounded is 5 to 20 parts by weight based on 100 parts by weight of the polymerizable monomer. More preferably, the amount of the (meth)acrylic acid group-containing polymerizable monomer to be compounded is 85 to 95 parts by weight and the amount of the hydrophilic polymerizable monomer to be compounded is 5 to 15 parts by weight.

The (meth)acrylic acid (co)polymer for use in the powder material of the dental powder-liquid type acrylic material of the present invention is a polymer or copolymer using the (meth)acrylic acid-containing polymerizable monomer described in the section of the polymerizable monomer above. Among them, a polymer or copolymer of methyl (meth)acrylate and/or ethyl (meth)acrylate is preferable, and a copolymer of methyl methacrylate and ethyl methacrylate is particularly preferable. The acrylic acid (co)polymer can be used singly or in combinations of a plurality thereof, without any problem.

The average molecular weight of such a (co)polymer is 500 or more. The average molecular weight is preferably 1,000 to 20,000, particularly preferably 3,000 to 10,000. The particle size is preferably 20 to 200 μm. The particle size and the shape are not particularly limited, and a powder shape is preferable.

In the dental powder-liquid type acrylic material of the present invention, the amount of 1-cyclohexyl-5-propylbarbituric acid to be compounded is preferably 0.1 to 10 parts by weight based on 100 parts by weight of the polymerizable monomer. 1-Cyclohexyl-5-propylbarbituric acid is preferably compounded in an amount of 0.5 to 5 parts by weight, further preferably 1 to 3 parts by weight. If the amount to be compounded is less than 0.1 parts by weight, a case may occur in which reactivity is poor and curability cannot be achieved. If the amount to be compounded is more than 10 parts by weight, the amount of heat generation in a polymerization reaction may be remarkably large regardless of a certain curing time.

A known organic solvent can be used, and can be compounded to thereby serve to reduce the viscosity of the kneaded product of the dental powder-liquid type acrylic material of the present invention, resulting in an enhancement in wettability to a denture base that is mounted in an oral cavity and absorbs water, in the case of repair of the denture base. As a specific organic solvent, methanol, ethanol, isopropanol, butanol, acetone, ethyl acetate, isopropyl ether or the like can be utilized. Methanol, ethanol or acetone is preferable, and ethanol is most preferable. The organic solvent can be included to thereby facilitate kneading with the powder material, exerting the effect of enhancing wettability to a wet base resin and wettability to a tooth substance. An excellent storage stability is also achieved.

The amount of the organic solvent to be compounded can be 0.5 to 20 parts by weight based on 100 parts by weight of the polymerizable monomer. The amount is preferably 1 to 5 parts by weight. If the amount of the organic solvent to be compounded is 0.5 parts by weight or less, the effect of reducing the viscosity of the liquid material and the effect of enhancing wettability are not largely exerted. On the other hand, if the amount of the organic solvent to be compounded is 20 parts by weight or more, deterioration in physical properties is caused.

The filler to be compounded to the powder material is not particularly limited, and a known filler can be used. The filler can be compounded to result in enhancements in wear resistance and bending property. As a specific example of the filler, an inorganic filler and/or an organic filler and/or an organic-inorganic composite filler can be used without any limitation. The shape of the filler may be any particle shape such as a spherical shape, a massive shape, a needle shape, a plate shape, a fracture shape, a scale-like shape or the like, and is not particularly limited. In order that the filler is compounded to the dental powder-liquid type acrylic material in a large amount, the filler preferably has a spherical shape. As a specific filler, the filler described in the section [dental material] above can be used.

Herein, the amount of the filler to be compounded is preferably 0.1 to 100 parts by weight based on 100 parts by weight of the monomer. Further preferably, the amount is 1 to 10 parts by weight.

The test methods for evaluating performances of the dental material of the present invention are as follows.

(Bending Test Method)

Object of evaluation: To evaluate bending strength of dental material specimen.

Evaluation method: A dental material prepared according to compounding shown in Table 1 was filled in a stainless steel mold, and thereafter left to stand for 1 hour and cured. After curing, a cured product was taken out from the mold, and thereafter burr and the like were removed to provide a specimen (25×2×2 mm: cuboid type). The specimen was immersed in water at 37° C. for 24 hours, and thereafter subjected to the bending test. This specimen was defined as the initial specimen. In addition, this specimen was immersed in water under a load of 10 kg to a face with a size of 25×2 mm at 37° C. for 30 days, and thereafter subjected to the bending test. This specimen was defined as the specimen after loading for 30 days.

The bending test was conducted at a distance between supporting points of 20 mm and at a crosshead speed of 1 mm/min using an Instron universal testing machine (Instron 5567 manufactured by Instron). Herein, the test was conducted for ten of the specimens, and evaluation was made by the average value for ten of the specimens.

(Compression Test Method)

Object of evaluation: To evaluate compressive strength of dental material specimen.

Evaluation method: A dental material prepared according to compounding shown in Table 1 was filled in a stainless steel mold, and thereafter left to stand for 1 hour and cured. After curing, a cured product was taken out from the mold, and thereafter burr and the like were removed to provide a specimen (having a diameter of 3 mm and a height of 6 mm: cylinder type). The specimen was immersed in water at 37° C. for 24 hours, and thereafter subjected to the compression test. This specimen was defined as the initial specimen. In addition, this specimen was immersed in water under a load of 10 kg to a face with a diameter of 3 mm at 37° C. for 30 days, and thereafter subjected to the compression test. This specimen was defined as the specimen after loading for 30 days.

The compression test was conducted at a crosshead speed of 1 mm/min using an Instron universal testing machine (Instron 5567, Instron). Herein, the test was conducted for ten of the specimens, and evaluation was made by the average value for ten of the specimens.

(Discolorability Test)

A dental material prepared according to compounding shown in Table 1 was filled in a 3 mm thick polyacetal mold having a through hole of a diameter of 8 mm, and both ends of the through hole were pressure-bonded by a polypropylene film and the resultant was left to stand for 5 hours to produce 6 cured articles (test pieces). The resulting test pieces were subjected to buffing of the surfaces thereof, and the samples after storage in water for 24 hours were defined as the initial immersed articles. Thereafter, 5 articles of the initial immersed articles were immersed in water at 80° C. for 7 days. After immersion, the articles were treated by washing with water and drying, and defined as test pieces treated, and the test pieces treated were relatively rated to the initial immersed article with respect to the degree of discoloration. The rating criteria are as follows. Five of the test pieces treated were produced and rated by three persons, and the rating most frequently given from the three persons was defined as the test result.

A: The degrees of discoloration of the test pieces treated were almost the same as the degrees of discoloration of the initial immersed article.

B: The degrees of discoloration of the test pieces treated were extremely slightly different from the degrees of discoloration of the initial immersed article.

C: The degrees of discoloration of the test pieces treated were slightly different from the degrees of discoloration of the initial immersed article.

D: The degrees of discoloration of the test pieces treated were clearly different from the degrees of discoloration of the initial immersed article.

The compounds shown in Table 1, used in Examples and Comparative Examples of the present invention, and the abbreviations thereof are shown below.

1-Cyclohexyl-5-propylbarbituric acid (Examples): CPBA
1-Cyclohexyl-5-methylbarbituric acid (Comparative Examples): CMBA
Polymerizable monomer: methyl methacrylate: MMA
Polymerizable monomer: 2-ethoxyethyl methacrylate: 2EEMA Polymerizable monomer (crosslinkable): 2,2-bis(4-methacryloyloxyphenyl)propane: BMFP
Polymerizable monomer (crosslinkable): 2-hydroxy-3-acryloyloxypropyl methacrylate: HAPM
Organometal compound: copper(II) acetylacetonate: CAA
Organometal compound: acetylacetone lithium: AAL
Organohalogen compound: trioctylmethylammonium chloride: TOMAC
Organohalogen compound: dilauryl dimethylammonium chloride: DLDMAC The amounts of compounds constituting the dental material used in each of the Examples and Comparative Examples of the present invention, to be compounded, and the test results are shown in Table 1 below.

TABLE 1

|  | Abbreviation | Example 1 | Example 2 | Example 3 | Example 4 | Example 5 | Example 6 | Example 7 | Example 8 |
|---|---|---|---|---|---|---|---|---|---|
|  | CPBA | 2 | 2 | 2 | 2 | 2 | 2 | 2 | 2 |
|  | CMBA |  |  |  |  |  |  |  |  |
| Polymerizable | MMA | 100 |  |  |  | 50 | 100 | 100 | 100 |
| monomer | 2EEMA |  | 100 |  |  | 50 |  |  |  |
|  | BMFP |  |  | 100 |  |  |  |  |  |
|  | HAPM |  |  |  | 100 |  |  |  |  |
| Organometal | CAA | 0.1 | 0.1 | 0.1 | 0.1 |  | 0.1 | 0.1 | 0.01 |
| compound | AAL |  |  |  |  | 0.1 |  |  |  |
| Organohalogen | TOMAC | 2 | 2 | 2 | 2 | 2 | 0.2 | 4 | 2 |
| compound | DLDMAC | 2 | 2 | 2 | 2 | 2 | 0.2 | 4 | 2 |
| Bending test | Initial test value | 105.6 | 108.0 | 102.9 | 110.2 | 104.7 | 102.8 | 108.1 | 104.2 |
| results (MPa) | After test under loading for 30 days | 104.4 | 107.5 | 101.8 | 108.7 | 104.5 | 101.5 | 107.1 | 103.5 |
| Bending test (initial value − value after test under loading for 30 days) |  | 1.2 | 0.5 | 1.1 | 1.5 | 0.2 | 1.3 | 1.0 | 0.7 |
| Compression test | Initial test value | 154.7 | 156.2 | 154.7 | 149.7 | 158.4 | 157.2 | 151.9 | 154.2 |
| result (MPa) | Afer test under loading for 30 days | 152.9 | 155.1 | 153.6 | 149.1 | 157.5 | 155.9 | 149.9 | 152.4 |
| Compression test (initial value − value after test under loading for 30 days) |  | 1.8 | 1.1 | 1.1 | 0.6 | 0.9 | 1.3 | 2.0 | 1.8 |
| Colorability test results |  | A | A | A | A | A | A | A | A |

|  | Abbreviation | Example 9 | Example 10 | Example 11 | Example 12 | Example 13 | Example 14 | Example 15 |
|---|---|---|---|---|---|---|---|---|
|  | CPBA | 2 | 1.2 | 2.8 | 0.3 | 4.5 | 2 | 2 |
|  | CMBA |  |  |  |  |  |  |  |
| Polymerizable | MMA | 100 | 100 | 100 | 100 | 100 | 100 | 100 |
| monomer | 2EEMA |  |  |  |  |  |  |  |
|  | BMFP |  |  |  |  |  |  |  |
|  | HAPM |  |  |  |  |  |  |  |
| Organometal | CAA | 0.2 | 0.1 | 0.1 | 0.1 | 0.1 | 0.01 | 0.01 |
| compound | AAL |  |  |  |  |  |  |  |
| Organohalogen | TOMAC | 2 | 0.5 | 4 | 2 | 2 | 0.15 | 8 |
| compound | DLDMAC | 2 | 0.5 | 4 | 2 | 2 | 0.15 | 8 |
| Bending test | Initial test value | 104.9 | 107.4 | 108.2 | 103.9 | 105.4 | 107.4 | 102.4 |
| results (MPa) | After test under loading for 30 days | 104.2 | 106.5 | 107.5 | 100.5 | 102.1 | 104.0 | 99.4 |
| Bending test (initial value − value after test under loading for 30 days) |  | 0.7 | 0.9 | 0.7 | 3.4 | 3.3 | 3.4 | 3.0 |
| Compression test | Initial test value | 156.4 | 152.4 | 154.7 | 157.2 | 149.4 | 152.7 | 156.2 |
| result (MPa) | Afer test under loading for 30 days | 154.8 | 151.3 | 153.4 | 154.1 | 146.5 | 149.5 | 153.1 |
| Compression test (initial value − value after test under loading for 30 days) |  | 1.6 | 1.1 | 1.3 | 3.1 | 2.9 | 3.2 | 3.1 |
| Colorability test results |  | A | A | A | B | B | B | B |

|  | Abbreviation | Example 16 | Example 17 | Example 18 | Example 19 | Example 20 | Example 21 |
|---|---|---|---|---|---|---|---|
|  | CPBA | 2 | 2 | 2 | 2 | 0.2 | 8 |
|  | CMBA |  |  |  |  |  |  |
| Polymerizable | MMA | 100 | 100 | 100 | 100 | 100 | 100 |
| monomer | 2EEMA |  |  |  |  |  |  |
|  | BMFP |  |  |  |  |  |  |
|  | HAPM |  |  |  |  |  |  |
| Organometal | CAA | 0.8 | 0.8 | 0.5 | 0.8 | 0.01 | 0.8 |
| compound | AAL |  |  |  |  |  |  |
| Organohalogen | TOMAC | 8 | 8 | 2 | 2 | 2 | 2 |
| compound | DLDMAC | 8 | 8 | 2 | 2 | 2 | 2 |
| Bending test | Initial test value | 105.9 | 106.8 | 105.1 | 103.2 | 102.8 | 105.7 |
| results (MPa) | After test under loading for 30 days | 101.5 | 102.4 | 101.9 | 99.8 | 97.8 | 100.2 |
| Bending test (initial value − value after test under loading for 30 days) |  | 4.3 | 4.4 | 3.2 | 3.4 | 5.0 | 5.5 |
| Compression test | Initial test value | 154.8 | 151.5 | 150.9 | 158.4 | 154.2 | 151.9 |
| result (MPa) | Afer test under loading for 30 days | 150.3 | 147.2 | 147.6 | 155.4 | 149.2 | 146.1 |
| Compression test (initial value − value after | | 4.5 | 43 | 3.3 | 3.0 | 5.0 | 5.8 |

TABLE 1-continued

| | | | | | | | | |
|---|---|---|---|---|---|---|---|---|
| test under loading for 30 days) | | | | | | | | |
| Colorability test results | | B | B | B | B | B | B | B | B |

| | Abbreviation | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|---|
| Polymerizable monomer | CPBA | | | | | | | | |
| | CMBA | 2 | 2 | 2 | 2 | 2 | 2 | 2 | 2 |
| | MMA | 100 | 100 | 50 | | 100 | 100 | 100 | 100 |
| | 2EEMA | | | 50 | | | | | |
| | BMFP | | | | 50 | | | | |
| | HAPM | | | | 50 | | | | |
| Organometal compound | CAA | 0.1 | 0.1 | 0.1 | 0.1 | | 0.1 | 0.1 | 0.01 |
| | AAL | | | | | 0.1 | | | |
| Organohalogen compound | TOMAC | 2 | 2 | | 2 | 2 | 0.2 | 4 | 2 |
| | DLDMAC | | | | | | | | |
| Bending test results (Mpa) | Initial specimen | 104.5 | 105.4 | 100.8 | 108.4 | 101.9 | 101.4 | 106.8 | 102.2 |
| | Specimen after loading for 30 days | 83.4 | 84.0 | 79.8 | 84.5 | 80.4 | 79.4 | 81.7 | 79.9 |
| Bending test (initial value − value after test under loading for 30 days) | | 21.1 | 21.4 | 21.0 | 23.9 | 21.5 | 22.0 | 25.1 | 22.3 |
| Compression test result (MPa) | Initial specimen | 150.4 | 151.4 | 149.4 | 145.1 | 148.2 | 149.7 | 151.4 | 148.9 |
| | Specimen after loading for 30 days | 118.5 | 120.1 | 117.4 | 115.0 | 114.2 | 114.8 | 117.6 | 113.9 |
| Compression test (initial value − value after test under loading for 30 days) | | 31.9 | 31.3 | 32.0 | 30.1 | 34.0 | 34.9 | 33.8 | 35.0 |
| Colorability test results | | C | C | C | C | C | C | C | C |

| | Abbreviation | Comparative Example 9 | Comparative Example 10 | Comparative Example 11 | Comparative Example 12 | Comparative Example 13 | Comparative Example 14 | Comparative Example 15 |
|---|---|---|---|---|---|---|---|---|
| Polymerizable monomer | CPBA | | | | | | | |
| | CMBA | 2 | 1.2 | 2.8 | 0.3 | 4.5 | 2 | 2 |
| | MMA | 100 | 100 | 100 | 100 | 100 | 100 | 100 |
| | 2EEMA | | | | | | | |
| | BMFP | | | | | | | |
| | HAPM | | | | | | | |
| Organometal compound | CAA | 0.2 | 0.1 | 0.1 | 0.1 | 0.1 | 0.01 | 0.01 |
| | AAL | | | | | | | |
| Organohalogen compound | TOMAC | 2 | 0.5 | 4 | 2 | 2 | 0.15 | 8 |
| | DLDMAC | | | | | | | |
| Bending test results (Mpa) | Initial specimen | 101.7 | 105.9 | 104.9 | 101.4 | 102.4 | 103.9 | 101.4 |
| | Specimen after loading for 30 days | 79.8 | 81.4 | 80.7 | 74.2 | 73.4 | 74.1 | 71.4 |
| Bending test (initial value − value after test under loading for 30 days) | | 21.9 | 24.5 | 24.2 | 27.2 | 29.0 | 29.8 | 30.0 |
| Compression test result (MPa) | Initial specimen | 150.4 | 149.6 | 147.9 | 152.4 | 145.8 | 147.4 | 150.9 |
| | Specimen after loading for 30 days | 115.0 | 112.9 | 114.8 | 111.4 | 104.7 | 104.8 | 110.1 |
| Compression test (initial value − value after test under loading for 30 days) | | 35.4 | 36.7 | 33.1 | 41.0 | 41.1 | 42.6 | 40.8 |
| Colorability test results | | C | C | C | C | C | C | C |

| | Abbreviation | Comparative Example 16 | Comparative Example 17 | Comparative Example 18 | Comparative Example 19 | Comparative Example 20 | Comparative Example 21 |
|---|---|---|---|---|---|---|---|
| Polymerizable monomer | CPBA | | | | | | |
| | CMBA | 2 | 2 | 2 | 2 | 0.2 | 8 |
| | MMA | 100 | 100 | 100 | 100 | 100 | 100 |
| | 2EEMA | | | | | | |
| | BMFP | | | | | | |
| | HAPM | | | | | | |
| Organometal compound | CAA | 0.8 | 0.8 | 0.5 | 0.8 | 0.01 | 0.8 |
| | AAL | | | | | | |
| Organohalogen compound | TOMAC | 8 | 8 | 2 | 2 | 2 | 2 |
| | DLDMAC | | | | | | |
| Bending test results (Mpa) | Initial specimen | 102.9 | 103.4 | 102.5 | 101.4 | 100.9 | 102.9 |
| | Specimen after loading for 30 days | 68.4 | 69.4 | 74.2 | 74.4 | 54.8 | 64.7 |
| Bending test (initial value − value after test under loading for 30 days) | | 34.5 | 34.0 | 28.3 | 27.0 | 36.1 | 38.2 |
| Compression test result (MPa) | Initial specimen | 151.7 | 148.6 | 146.8 | 153.7 | 146.7 | 145.7 |
| | Specimen after loading for 30 days | 108.4 | 105.7 | 110.5 | 110.8 | 102.4 | 101.9 |

TABLE 1-continued

| | | | | | | | |
|---|---|---|---|---|---|---|---|
| Compression test (initial value – value after test under loading for 30 days) | 43.3 | 42.9 | 36.3 | 42.9 | 44.3 | 43.8 |
| Colorability test results | C | C | C | C | C | C |

| | Abbreviation | Comparative Example 22 | Comparative Example 23 | Comparative Example 24 | Comparative Example 25 | Comparative Example 26 | Comparative Example 27 | Comparative Example 28 | Comparative Example 29 |
|---|---|---|---|---|---|---|---|---|---|
| | CPBA | 2 | 2 | 2 | 2 | 2 | 2 | 2 | 2 |
| | CMBA | | | | | | | | |
| Polymerizable monomer | MMA | 100 | 100 | 50 | | 100 | 100 | 100 | 100 |
| | 2EEMA | | | 50 | | | | | |
| | BMFP | | | | 50 | | | | |
| | HAPM | | | | 50 | | | | |
| Organometal compound | CAA | 0.1 | 0.1 | 0.1 | 0.1 | | 0.1 | 0.1 | 0.01 |
| | AAL | | | | | 0.1 | | | |
| Organohalogan compound | TOMAC | | | | | | | | |
| | DLDMAC | 2 | 2 | | 2 | 2 | 0.2 | 4 | 2 |
| Bending test results (MPa) | Initial specimen | 103.6 | 104.9 | 102.5 | 104.9 | 102.5 | 100.5 | 106.9 | 101.9 |
| | Specimen after loading for 30 days | 83.3 | 84.2 | 83.5 | 85.1 | 82.1 | 79.5 | 86.3 | 80.1 |
| Bending test (initial value – value after test under loading for 30 days) | | 20.3 | 20.7 | 19.0 | 19.8 | 20.4 | 21.0 | 20.6 | 21.8 |
| Compression test results (MPa) | Initial specimen | 151.3 | 150.4 | 150.1 | 148.2 | 149.7 | 151.2 | 154.9 | 148.7 |
| | Specimen after loading (or 30 days | 122.3 | 119.9 | 119.7 | 117.9 | 119.8 | 122.1 | 123.9 | 119.4 |
| Compression test (initial value – value after test under loading for 30 days) | | 29.0 | 30.5 | 30.4 | 30.3 | 29.9 | 29.1 | 31.0 | 29.3 |
| Colorability test results | | C | C | C | C | C | C | C | C |

| | Abbreviation | Comparative Example 30 | Comparative Example 31 | Comparative Example 32 | Comparative Example 33 | Comparative Example 34 | Comparative Example 35 | Comparative Example 36 |
|---|---|---|---|---|---|---|---|---|
| | CPBA | 2 | 1.2 | 2.8 | 0.3 | 4.5 | 2 | 2 |
| | CMBA | | | | | | | |
| Polymerizable monomer | MMA | 100 | 100 | 100 | 100 | 100 | 100 | 100 |
| | 2EEMA | | | | | | | |
| | BMFP | | | | | | | |
| | HAPM | | | | | | | |
| Organometal compound | CAA | 0.2 | 0.1 | 0.1 | 0.1 | 0.1 | 0.01 | 0.01 |
| | AAL | | | | | | | |
| Organohalogan compound | TOMAC | | | | | | | |
| | DLDMAC | 2 | 0.5 | 4 | 2 | 2 | 0.15 | 8 |
| Bending test results (MPa) | Initial specimen | 102.5 | 104.2 | 105.1 | 102.0 | 102.3 | 103.5 | 101.9 |
| | Specimen after loading for 30 days | 81.2 | 83.6 | 85.4 | 77.1 | 77.5 | 78.3 | 76.5 |
| Bending test (initial value – value after test under loading for 30 days) | | 21.3 | 20.6 | 19.7 | 24.9 | 24.8 | 25.2 | 25.4 |
| Compression test results (MPa) | Initial specimen | 148.6 | 156.4 | 158.2 | 156.8 | 147.9 | 148.3 | 151.3 |
| | Specimen after loading (or 30 days | 119.2 | 128.4 | 129.4 | 116.4 | 105.9 | 107.9 | 112.0 |
| Compression test (initial value – value after test under loading for 30 days) | | 29.4 | 28.0 | 28.8 | 40.4 | 42.0 | 40.4 | 39.3 |
| Colorability test results | | C | C | C | C | C | C | C |

| | Abbreviation | Comparative Example 37 | Comparative Example 38 | Comparative Example 39 | Comparative Example 40 | Comparative Example 41 | Comparative Example 42 |
|---|---|---|---|---|---|---|---|
| | CPBA | 2 | 2 | 2 | 2 | 0.2 | 8 |
| | CMBA | | | | | | |
| Polymerizable monomer | MMA | 100 | 100 | 100 | 100 | 100 | 100 |
| | 2EEMA | | | | | | |
| | BMFP | | | | | | |
| | HAPM | | | | | | |
| Organometal compound | CAA | 0.8 | 8 | 0.5 | 0.8 | 0.01 | 0.8 |
| | AAL | | | | | | |
| Organohalogan compound | TOMAC | | | | | | |
| | DLDMAC | 8 | 8 | 2 | 2 | 2 | 2 |
| Bending test results (MPa) | Initial specimen | 102.8 | 103.6 | 103.1 | 102.0 | 101.2 | 101.9 |
| | Specimen after loading for 30 days | 74.2 | 75.3 | 78.2 | 75.9 | 71.5 | 70.4 |
| Bending test (initial value – value after test under loading for 30 days) | | 28.6 | 28.3 | 24.9 | 26.1 | 29.7 | 31.5 |

TABLE 1-continued

| | | | | | | | |
|---|---|---|---|---|---|---|---|
| Compression test results (MPa) | Initial specimen | 152.9 | 149.8 | 154.8 | 148.7 | 143.2 | 143.9 |
| | Specimen after loading (or 30 days) | 105.9 | 102.2 | 113.2 | 109.6 | 92.5 | 90.9 |
| Compression test (initial value − value after test under loading for 30 days) | | 47.0 | 47.6 | 41.6 | 39.1 | 50.7 | 53.0 |
| Colorability test results | | C | C | C | C | C | C |

(Part(s) by weight)

In the Examples, the value after the bending test under loading for 30 days was reduced from the initial value in the bending test by only at most 5.5 MPa, and the value after the compression test under loading for 30 days was reduced from the initial value in the compression test by only at most 5.8 MPa.

In the Comparative Examples, the value after the bending test under loading for 30 days was reduced from the initial value in the bending test by even at least 19.0 MPa, and the value after the compression test under loading for 30 days was reduced from the initial value in the compression test by even at least 28 MPa.

The reductions in the strengths were clearly less observed in the Examples than in the Comparative Examples.

The test methods for evaluating performances of the dental powder-liquid type acrylic material of the present invention are as follows.

(Adhesion Bending Strength Test Method)

Object of evaluation: To evaluate adhesion bending strength to general-purpose dental acrylic resin.

Evaluation method: A test piece 1 (10×2×2 mm: cuboid) was produced by a general-purpose dental acrylic resin (Adfa: manufactured by Shofu Inc.), and immersed in water at 37° C. for 7 days to prepare a test piece. Such test pieces 1 were secured with a gap of 5 mm disposed therebetween. Next, a powder material and a liquid material prepared according to compounding shown in Table 2 were kneaded in a predetermined ratio to prepare a kneaded product 2 of a dental powder-liquid type acrylic material. The gap of 5 mm disposed between the test pieces 1 was filled therewith using a brush. After filling, the resultant was left to stand for 1 hour, and burr and the like were removed to provide a specimen (25×2×2 mm: cuboid type) (see FIG. 1). The specimen was immersed in water at 37° C. for 24 hours, and thereafter subjected to the adhesion bending strength test.

The adhesion bending strength test was conducted at a distance between supporting points of 20 mm and at a crosshead speed of 1 mm/min using an Instron universal testing machine (Instron 5567 manufactured by Instron). Herein, the test was conducted for ten of the specimens, and evaluation was made by the average value for ten of the specimens.

(Filling Test Method)

Object of evaluation: To evaluate wettability and fillability to and with wet general-purpose dental acrylic resin.

Evaluation method: The filling test was conducted at the same time as the timing where "the gap of 5 mm disposed between the test pieces was filled therewith" in the adhesion bending strength test method. The rating criteria are as follows.

A: The gap between the test pieces could be filled with the kneaded product without any space, and the brush was favorably released.

B: While bubbles were slightly generated at the corner of the gap between the test pieces, the brush was favorably released.

C: Bubbles were generated at the corner of the gap between the test pieces, and also the brush was not favorably released.

(Curability Test Method)

Object of evaluation: To evaluate operation time of kneaded product of dental powder-liquid type acrylic material.

Evaluation method: A powder material and a liquid material prepared according to compounding shown in Table 2 were kneaded in a specified kneading ratio for 30 seconds, and thereafter 0.5 ml of a rice cake-like kneaded product was taken and placed on about 20 g of a glass plate, and left to still stand for 30 seconds. One more glass plate having the same size as above was placed on the kneaded product, and furthermore 100 g of a weight was gently placed thereon. After the weight was placed, the weight was removed at 30 seconds after initiation, and expansion of the circularity was calculated as the average value of the maximum and minimum diameters and was defined as the flow value. A larger flow value was determined as better fluidity. Such a procedure was performed and the change in fluidity was confirmed at standing times of 30 seconds, 60 seconds, 120 seconds and 180 seconds. The rating criteria of the amount of the change were defined based on the flow value at a standing time of 30 seconds and as follows. A case where the flow value at a standing time of 120 seconds was 90% or more and the flow value at a standing time of 150 seconds was 50% or less was rated as (A) because suitable operation time and curing time were achieved, a case where the flow value at a standing time of 120 seconds was less than 90% was rated as (B) because the operation time was too short, and a case where the flow value at a standing time of 150 seconds was more than 50% was rated as (C) because the curing time was too long.

(Discolorability Test)

Object of evaluation: To evaluate degree of discoloration of cured article of dental powder-liquid type acrylic material.

Evaluation method: A powder material and a liquid material prepared according to compounding shown in Table 2 were kneaded in a specified kneading ratio for 30 seconds, the resulting kneaded product was filled in a 3 mm thick polyacetal mold having a through hole of a diameter of 8 mm, and both ends of the through hole were pressure-bonded by a polypropylene film and the resultant was left to stand for 5 hours to produce 6 test pieces. The resulting test pieces were subjected to buffing of the surfaces thereof, and the samples after storage in water for 24 hours were defined as the initial immersed articles. Thereafter, 5 articles of the initial immersed articles were immersed in water at 80° C. for 7 days. After immersion, the articles were treated by washing with water and drying, and defined as test pieces treated, and the test pieces treated were relatively rated to the initial immersed article with respect to the degree of discoloration. The rating criteria are as follows. Five of the test pieces treated were produced and rated by three persons, and the rating most frequently given from the three persons was defined as the test result.
A: The degrees of discoloration of the test pieces treated were the same as the degrees of discoloration of the initial immersed article.
B: The degrees of discoloration of the test pieces treated were slightly different from the degrees of discoloration of the initial immersed article.
C: The degrees of discoloration of the test pieces treated were clearly different from the degrees of discoloration of the initial immersed article.

The compounds shown in the Examples and Comparative Examples of the present invention, and the abbreviations thereof are shown below.
<Liquid Material Components>
(Meth)acrylic acid group-containing monomer: methyl methacrylate [MMA]
(Meth)acrylic acid group-containing monomer: 2-ethoxyethyl methacrylate [2EEMA]
(Meth)acrylic acid group-containing monomer (crosslinkable): 1,6-hexanediol di(meth)acrylate [HDDMA]
(Meth)acrylic acid group-containing monomer (crosslinkable): 2-hydroxy-3-acryloyloxypropyl methacrylate [HAPM]
Hydrophilic monomer: 2-hydroxyethyl methacrylate [HEMA]
Organohalogen compound: trioctylmethylammonium chloride [TOMAC]
Organohalogen compound: dilauryl dimethylammonium chloride [DLDMAC]
Organic solvent: ethanol [Et]
<Powder Material Components>
Acrylic acid (co)polymer: polymethyl methacrylate [PMMA]
Organometal compound: copper(II) acetylacetonate [CAA]
Organometal compound: acetylacetone lithium [AAL]
1-Cyclohexyl-5-propylbarbituric acid [CPBA] (Examples)
1-Cyclohexyl-5-methylbarbituric acid [CMBA] (Comparative Examples)

The amounts of compounds constituting the dental material used in each of the Examples and Comparative Examples of the present invention, to be compounded, and the test results are shown in Table 2 below.

TABLE 2

| Powder or Liquid | Component | Abbreviation | Example 22 | Example 23 | Example 24 | Example 25 | Example 26 | Example 27 | Example 28 | Example 29 |
|---|---|---|---|---|---|---|---|---|---|---|
| Liquid | Monomer | MMA | 70 | 70 | 70 | 70 | 70 | 80 | 75 | |
|  |  | 2EEMA |  |  |  |  |  |  |  | 70 |
|  |  | HDDMA | 20 | 20 | 20 | 20 | 20 | 5 | 5 | |
|  |  | HAPM |  |  |  |  |  |  |  | 20 |
|  | Hydrophilic monomer | HEMA | 10 | 10 | 10 | 10 | 10 | 15 | 20 | 10 |
|  | Organic solvent | Et | 2.5 | 2.5 | 2.5 | 2.5 | 2.5 | 2.5 | 2.5 | 2.5 |
|  | Organohalogen compound | TOMAC | 2 | 5 | 8 | 0.5 | 0.2 | 2 | 2 | 2 |
| Powder | Acrylic acid copolymer | PMMA | 100 | 100 | 100 | 100 | 100 | 100 | 100 | 100 |
|  | Barbituric acid | CPBA | 2 | 5 | 8 | 0.5 | 0.3 | 2 | 1.2 | 2 |
|  |  | CMBA |  |  |  |  |  |  |  | |
|  | Organometal compound | CAA | 0.1 | 0.1 | 0.5 | 0.1 | 0.01 | 0.2 | 0.1 | 0.1 |
|  |  | AAL |  |  |  |  |  |  |  | |
| Mixing ratio (liquid:powder) | | | 1:1 | 1:1 | 1:1 | 1:1 | 1:1 | 1:1 | 1:1 | 1:0.9 |
| Test results | Adhesion bending strength test results (MPa) | | 75.4 | 73.5 | 71.6 | 72.6 | 64.2 | 71.5 | 72.5 | 72.1 |
|  | Filling test | | A | A | A | A | A | A | A | A |
|  | Curability test | | A | A | A | A | A | A | A | A |
|  | Discolorability test | | A | A | A | A | A | A | A | A |

| Powder or Liquid | Component | Abbreviation | Example 30 | Example 31 | Example 32 | Example 33 | Example 34 | Example 35 | Example 36 | Example 37 | Example 38 |
|---|---|---|---|---|---|---|---|---|---|---|---|
| Liquid | Monomer | MMA | 100 | 70 | 70 |  | 100 | 70 | 70 | 70 | 70 |
|  |  | 2EEMA |  |  |  | 70 |  |  |  |  | |
|  |  | HDDMA |  | 20 | 20 |  |  | 20 | 20 | 20 | 20 |
|  |  | HAPM |  |  |  | 20 |  |  |  |  | |
|  | Hydrophilic monomer | HEMA |  | 10 | 10 | 10 |  | 10 |  |  | |
|  | Organic solvent | Et | 2 | 1 | 5 | 2.5 | 2 |  |  | 0.1 | 30 |
|  | Organohalogen compound | TOMAC | 8 | 2 | 2 | 2 | 8 | 4 | 0.15 | 0.15 | 0.15 |
| Powder | Acrylic acid copolymer | PMMA | 100 | 100 | 100 | 100 | 100 | 100 | 100 | 100 | 100 |
|  | Barbituric acid | CPBA | 2 | 0.3 | 4.5 | 2 | 2 | 2.8 | 2 | 2 | 2 |
|  |  | CMBA |  |  |  |  |  |  |  |  | |
|  | Organometal compound | CAA | 0.8 | 0.1 | 0.1 | 0.1 | 0.8 | 0.1 | 0.01 | 0.01 | 0.01 |
|  |  | AAL |  |  |  |  |  |  |  |  | |
| Mixing ratio (liquid:powder) | | | 1:1.1 | 1:1 | 1:1 | 1:0.85 | 1:1.15 | 1:1 | 1:1 | 1:1 | 1:1 |
| Test results | Adhesion bending strength test results (MPa) | | 71.9 | 65.3 | 64.2 | 63.2 | 63.0 | 61.6 | 62.8 | 63.8 | 59.5 |
|  | Filling test | | B | A | A | A | B | A | C | B | A |
|  | Curability test | | A | B | C | C | B | B | A | A | B |
|  | Discolorability test | | A | A | A | A | A | A | A | A | A |

| Powder or Liquid | Component | Abbreviation | Comparative Example 43 | Comparative Example 44 | Comparative Example 45 | Comparative Example 46 | Comparative Example 47 |
|---|---|---|---|---|---|---|---|
| Liquid | Monomer | MMA | 70 | 70 | 70 | 70 | 70 |
|  |  | 2EEMA |  |  |  |  | |

TABLE 2-continued

|  |  |  | | | | | |
|---|---|---|---|---|---|---|---|
| | | HDDMA | 20 | 20 | 20 | 20 | 20 |
| | | HAPM | | | | | |
| | Hydrophilic monomer | HEMA | 10 | 10 | 10 | 10 | 10 |
| | Organic solvent | Et | 2.5 | 2.5 | 2.5 | 2.5 | 2.5 |
| | Organohalogen compound | TOMAC | 2 | 2 | 2 | 20 | 0.01 |
| Powder | Acrylic acid copolymer | PMMA | 100 | 100 | 100 | 100 | 100 |
| | Barbituric acid | CPBA | | | | 20 | 0.01 |
| | | CMBA | 2 | 8 | 0.5 | | |
| | Organometal compound | CAA | | | | 5 | 0.0001 |
| | | AAL | 0.1 | 0.1 | 0.1 | | |
| Mixing ratio (liquid:powder) | | | 1:1 | 1:1 | 1:1 | 1:1 | 1:1 |
| Test results | Adhesion bending strength test results (MPa) | | 52.4 | 51.9 | 50.3 | 42.3 | Uncured |
| | Filling test | | B | B | B | B | — |
| | Curability test | | C | B | C | C | — |
| | Discolorability test | | C | C | C | C | — |

(Part(s) by weight)

Example 22 imparted the most suitable configuration, and exhibited a high strength of 75.4 MPa in the adhesion bending strength test and also achieved high ratings: A in the filling test, A in the curability test and A in the discolorability test.

Examples 23 and 24, and Examples 25 and 26 exhibited a slight reduction in strength in the adhesion bending strength test because the amount of the catalyst was slightly large and the amount of the catalyst was slightly small, respectively, as compared with Example 22, but achieved high ratings: A in the filling test, A in the curability test and A in the discolorability test.

Examples 27, 28 and 29, in which the type and the amount of the monomer, and the kneading ratio of the powder and the liquid were changed, exhibited a slight reduction in strength in the adhesion bending strength test as compared with Example 22, but achieved high ratings in all the tests: A in the filling test, A in the curability test and A in the discolorability test.

In Examples 30 to 38, the amounts of the organic solvent and the hydrophilic monomer to be compounded, the kneading ratio of the powder and the liquid, and the like were changed. In Examples 31, 32, 33, 35 and 38 in which the amounts of the organic solvent and the hydrophilic monomer to be compounded were large, no reduction in fillability was observed. In Examples 30, 34 and 37 in which the amounts of the organic solvent and the hydrophilic monomer to be compounded were small, the rating of fillability was B and the kneaded product of the dental powder-liquid type acrylic material was released from the brush, but bubbles were generated in the gap between the test pieces and/or the kneaded product was not compatible with the test pieces in some cases, and thus the cured product was remade in some cases. In addition, in Example 36 in which no organic solvent and no hydrophilic monomer were included, the kneaded product of the dental powder-liquid type acrylic material was attached to the brush and was hardly filled in the gap of 5 mm between the test pieces.

Comparative Examples 43, 44 and 45, in which a different catalyst was utilized, exhibited a low strength of 50.3 to 52.4 MPa in the adhesion bending strength test, and also achieved low ratings in all the tests: B in the filling test, C in the curability test and C in the discolorability test.

In Comparative Example 46, the amount of the catalyst was large, and good test results were not obtained. In Comparative Example 47, the amount of the catalyst was small, and curing was not achieved.

The present invention is an invention that can be used in a dental material and that can be industrially applied.

BRIEF DESCRIPTION OF THE DRAWING

FIG. 1 is a schematic view of a device that characterizes the dental prosthetic appliance material of the present invention.

The present invention is an invention that can be used in a dental material and that can be industrially applied.

What is claimed is:

1. A dental material comprising a polymerizable monomer, 1-cyclohexyl-5-propylbarbituric acid and trioctylmethylammonium chloride, wherein the polymerizable monomer comprises a (meth)acrylic acid group-containing monomer.

2. The dental material according to claim 1, further comprising an organometal compound.

3. The dental material according to claim 1, comprising 0.1 to 10 parts by weight of 1-cyclohexyl-5-propylbarbituric acid and 0.1 to 10 parts by weight of trioctylmethylammonium chloride based on 100 parts by weight of the polymerizable monomer.

4. The dental material according to claim 2, comprising 0.1 to 10 parts by weight of 1-cyclohexyl-5-propylbarbituric acid, 0.1 to 10 parts by weight of trioctylmethylammonium chloride and 0.001 to 1 part by weight of the organometal compound based on 100 parts by weight of the polymerizable monomer.

5. The dental material according to claim 4, further comprising a filler.

6. The dental material according to claim 2, wherein the dental material is a dental powder-liquid acrylic material in which a liquid material and a powder material are kneaded and used, the liquid material comprises 100 parts by weight of the polymerizable monomer and 0.1 to 10 parts by weight of trioctylmethylammonium chloride, and the powder material comprises 70 to 130 parts by weight of a (meth)acrylic acid (co)polymer, 0.001 to 1 part by weight of the organometal compound and 0.1 to 10 parts by weight of 1-cyclohexyl-5-propylbarbituric acid.

7. The dental material according to claim 6, wherein the monomer in the liquid material further comprises a hydrophilic monomer.

8. The dental material according to claim 6, wherein the liquid material comprises 0.5 to 20 parts by weight of an organic solvent based on 100 parts by weight of the monomer.

9. The dental material according to claim 6, wherein the powder material further comprises a filler.

10. The dental material according to claim 7, wherein the liquid material comprises 0.5 to 20 parts by weight of an organic solvent based on 100 parts by weight of the monomer.

11. The dental material according to claim 7, wherein the powder material further comprises a filler.

* * * * *